United States Patent

Bremer et al.

[11] Patent Number: 4,475,550
[45] Date of Patent: Oct. 9, 1984

[54] HALO FOR STEREOTAXIC APPLICATIONS

[75] Inventors: Paul W. Bremer; Ross L. Bremer; P. Levon Pentecost, all of Jacksonville, Fla.

[73] Assignee: Bremer Orthopedics, Inc., Jacksonville, Fla.

[21] Appl. No.: 363,556

[22] Filed: Mar. 30, 1982

[51] Int. Cl.$^3$ .............................................. A61B 17/00
[52] U.S. Cl. .................................................. 128/303 B
[58] Field of Search .................... 128/303 B, 630, 659, 128/660

[56] References Cited

U.S. PATENT DOCUMENTS

| | | | |
|---|---|---|---|
| 1,129,333 | 2/1915 | Clarke | 128/303 B |
| 1,398,842 | 11/1921 | Cruse | 128/303 B |
| 3,508,552 | 4/1970 | Hainault | 128/303 B |
| 4,341,220 | 7/1982 | Perry | 128/303 B X |

FOREIGN PATENT DOCUMENTS

| | | | |
|---|---|---|---|
| 2139433 | 2/1973 | Fed. Rep. of Germany | 128/303 B |
| 527189 | 6/1977 | U.S.S.R. | 128/303 B |

OTHER PUBLICATIONS

Thompson, Aug. 1962, "Journal of Bone and Joint Surgery;" pp. 655-661.
Nickel et al., 10/1968, "Journal of Bone and Joint Surgery;" pp. 1400-1409.
Houtkin et al., 6/1972, "Journal of Bone and Joint Surgery;" pp. 881-883.
Pieron et al., 2/1970, "Journal of Bone and Joint Surgery;" pp. 119-123.
"Radionics" brochure, Type BRW CT Stereotaxic Guide.
Leksell et al., "Deep Brain Surgery"; 6/1977, brochure.
Houdek et al., "Small Radiation Fields . . . ".

Primary Examiner—Stephen C. Pellegrino
Attorney, Agent, or Firm—Cushman, Darby & Cushman

[57] ABSTRACT

A special halo assembly is used with a stereotaxic device including a frame having four radiolucent substantially planar walls with radiopague indicia formed on the walls, and is operatively fixed to the frame walls by brackets to positively position the halo assembly in a predetermined position with respect to the walls. The frame is fixed with respect to a radiotherapy machine or a CT scanner. The halo assembly includes a number of brackets each having a first portion fixed to the ring component of the assembly, and a second substantially planar portion extending radially outwardly from the ring component. A method of practicing radiotherapy on a patient having a brain lesion or the like is accomplished utilizing the device. The halo assembly is surgically affixed to the patient's head to be maintained in place until all radiotherapy sessions for the patient are completed. The stereotaxic guide is fixed in a CT scanner to determine the exact position of the brain lesion, and that information is inputted to the radiotherapy machine and the stereotaxic guide is positively positioned in the radiotherapy machine so that effective treatment of the patient takes place. The patient continues to wear the halo assembly, but not the guide, between therapy sessions.

6 Claims, 5 Drawing Figures

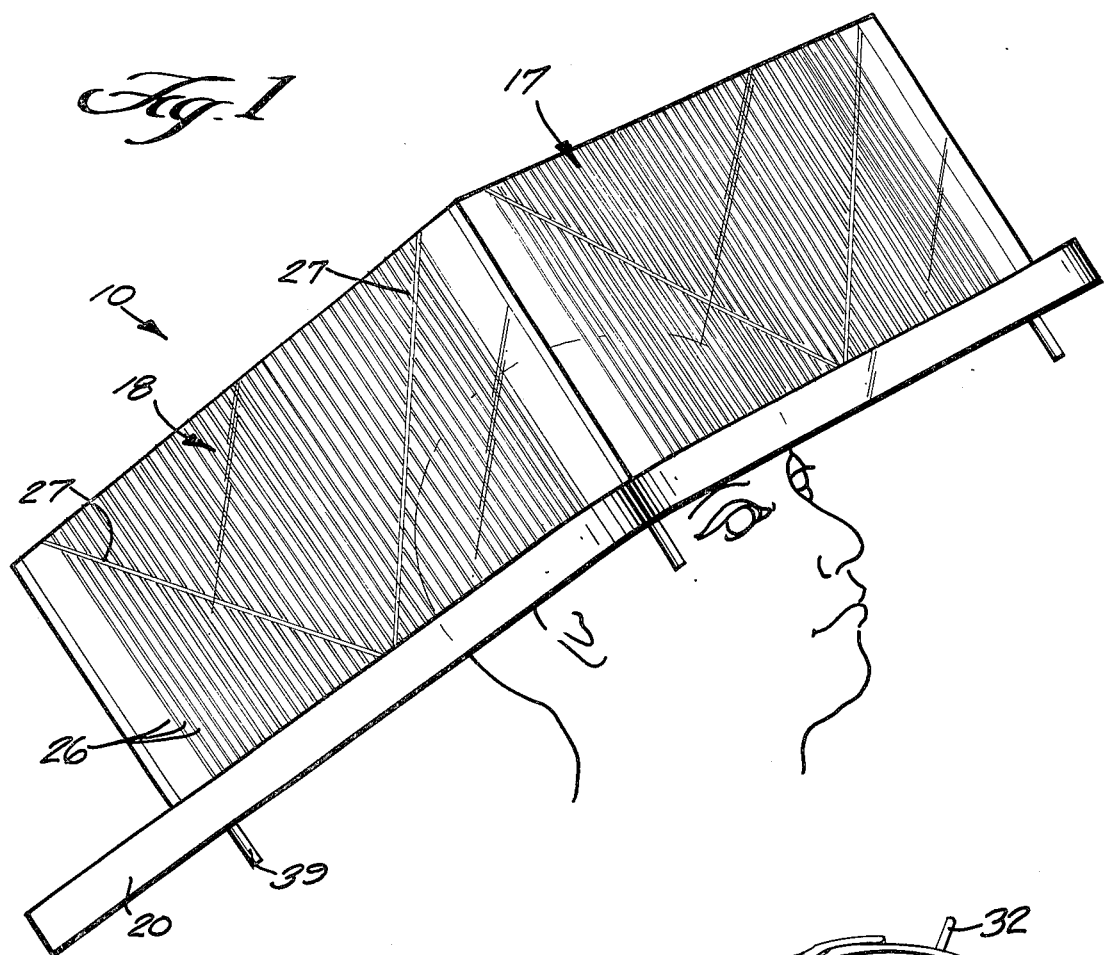
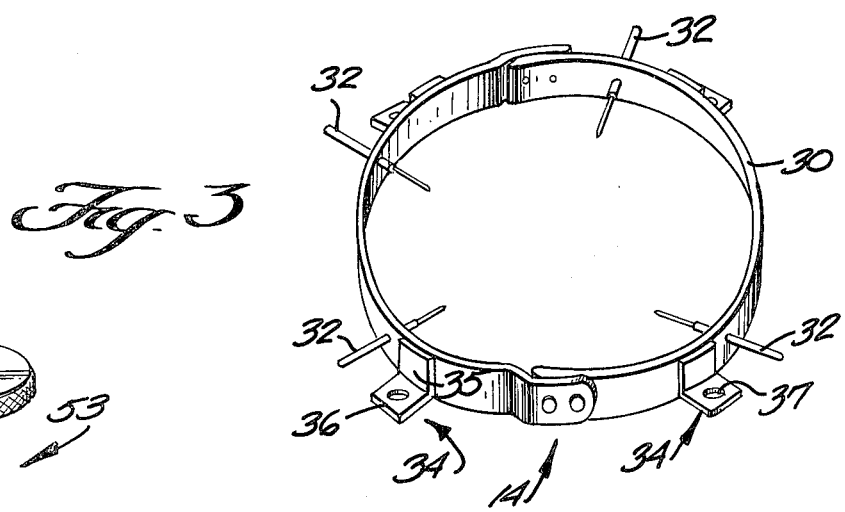
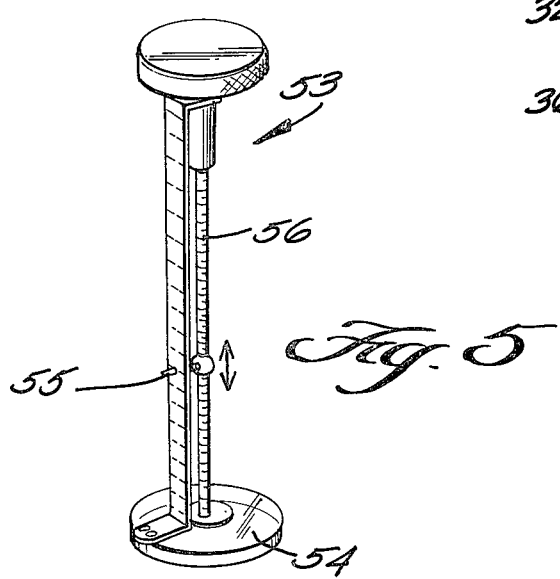

HALO FOR STEREOTAXIC APPLICATIONS

BACKGROUND AND SUMMARY OF THE INVENTION

In the treatment of intracranial lesions with radiation, a number of practical difficulties exist in conventional procedures. In such treatments, it is necessary for the treatment beams to be accurately aimed in all treatment sessions in order to treat effectively with minimum adverse peripheral consequences. In order to insure accurate repeatability, it is necessary to positively fix the patient's head with respect to the radiotherapy machine and/or a CT scanner, and the mechanisms for accomplishing this have been unwieldy and require removal and reattachment from treatment session to treatment session. Because of limitations inherent in conventional procedures, it is difficult to effectively treat by radiotherapy extremely small intracranial lesions (i.e. smaller than 4×4 centimeters), although treatment of such lesions would be extremely advantageous in effecting total patient care.

According to the present invention a halo assembly is provided, for use with a stereotaxic device, which eliminates or minimizes most of the drawbacks associated with current devices and procedures. Utilizing the halo assembly, with stereotaxic device, according to the invention, a method of practicing radiotherapy on a patient having an intracranial lesion or the like is provided which is substantially more simplified and/or more accurate than conventional methods.

The preferred stereotaxic device with which the invention is utilized includes a frame having four radiolucent substantially planar walls arranged in a quadrate in plan view. Radiopaque indicia means are formed on each of the walls. The halo assembly comprises a conventional halo for treatment of cervical fractures, with means for operatively fixing the position of the halo assembly to the frame walls to positively position the halo assembly in a predetermined position with respect to the walls. Also, means are provided for fixing the frames with respect to a radiotherapy machine. Preferably the frame also includes a substantially planar base plate substantially perpendicular to the walls, and means defining a through passage in the base plate, interior of a volume defined by the walls, for receipt of the halo assembly. Fixation of the halo assembly to the frame is preferably accomplished utilizing a plurality of brackets, each bracket having a first portion affixed to the ring component of the halo assembly, and a second substantially planar portion extending radially outwardly from the ring component of the halo assembly, the second portions being substantially coplanar.

The invention also comprises a method of practicing radiotherapy (rotational or a fixed source) on a patient having an intracranial lesion or the like. The method comprises the following sequential steps: (a) Determining the approximate position of the intracranial lesion or the like in the patient's head. (b) Surgically affixing a halo assembly to the patient's head to be maintained in place until all radiotherapy sessions for the patient are completed, taking care to position the ring component of the halo assembly with respect to the patient's skull so that effective treatment with radiation will be practiced. (c) Positioning the halo assembly in, and fixing it to, a stereotaxic guide having radiopaque indicia associated therewith. (d) Fixing the stereotaxic guide in a CT scanner. (e) Operating the CT scanner to determine the exact position of the intracranial lesion or the like with respect to the indicia provided by the stereotaxic guide. (f) Transferring the patient to a radiotherapy machine. (g) Fixing the stereotaxic guide with respect to the radiotherapy machine. (h) Inputting the coordinates of the intracranial lesion or the like, determined from the CT scan, to the radiotherapy machine. (i) Operating the radiotherapy machine to provide one treatment session for the patient, positioned in the stereotaxic guide in the radiotherapy machine. (j) Removing the halo assembly from the stereotaxic guide. (k) Replacing the stereotaxic guide on the halo assembly when the patient returns for the next treatment session, the halo assembly remaining in place on the patient between treatment sessions. (l) Repeating steps (g) through (k) until all desired radiotherapy sessions for the patient are completed; and (m) removing the halo assembly from the patient's head.

Step (a) is preferably practiced utilizing a CT scanner. Also, as a further step (n) between steps (f) and (g), the patient is removed from the stereotaxic guide, and as further steps between steps (g) and (i), (o) proper position of the radiotherapy machine with respect to the intracranial lesion is tested utilizing a target device in the stereotaxic guide, and the relative position of the radiotherapy machine is adjusted if necessary; and (p) the halo assembly is fixed in the stereotaxic guide, and step (l) further comprises repeating steps (n) through (p) for each session.

It is the primary object of the present invention to provide for the simple and effective radiotherapy of patients having an intracranial lesion or the like. This and other objects of the invention will become clear from an inspection of the detailed description of the invention, and from the appended claims.

BRIEF DESCRIPTION OF THE DRAWINGS

FIG. 1 is a perspective view of an exemplary stereotaxic device for use in practicing the present invention, shown in place on a patient's head;

FIG. 3 is a perspective view of a special halo assembly according to the present invention, utilized in the stereotaxic device of FIGS. 1 and 2;

FIG. 5 is a perspective view of an exemplary movable target member utilizable with the structure of FIG. 4.

DETAILED DESCRIPTION OF THE DRAWINGS

Figure 2:
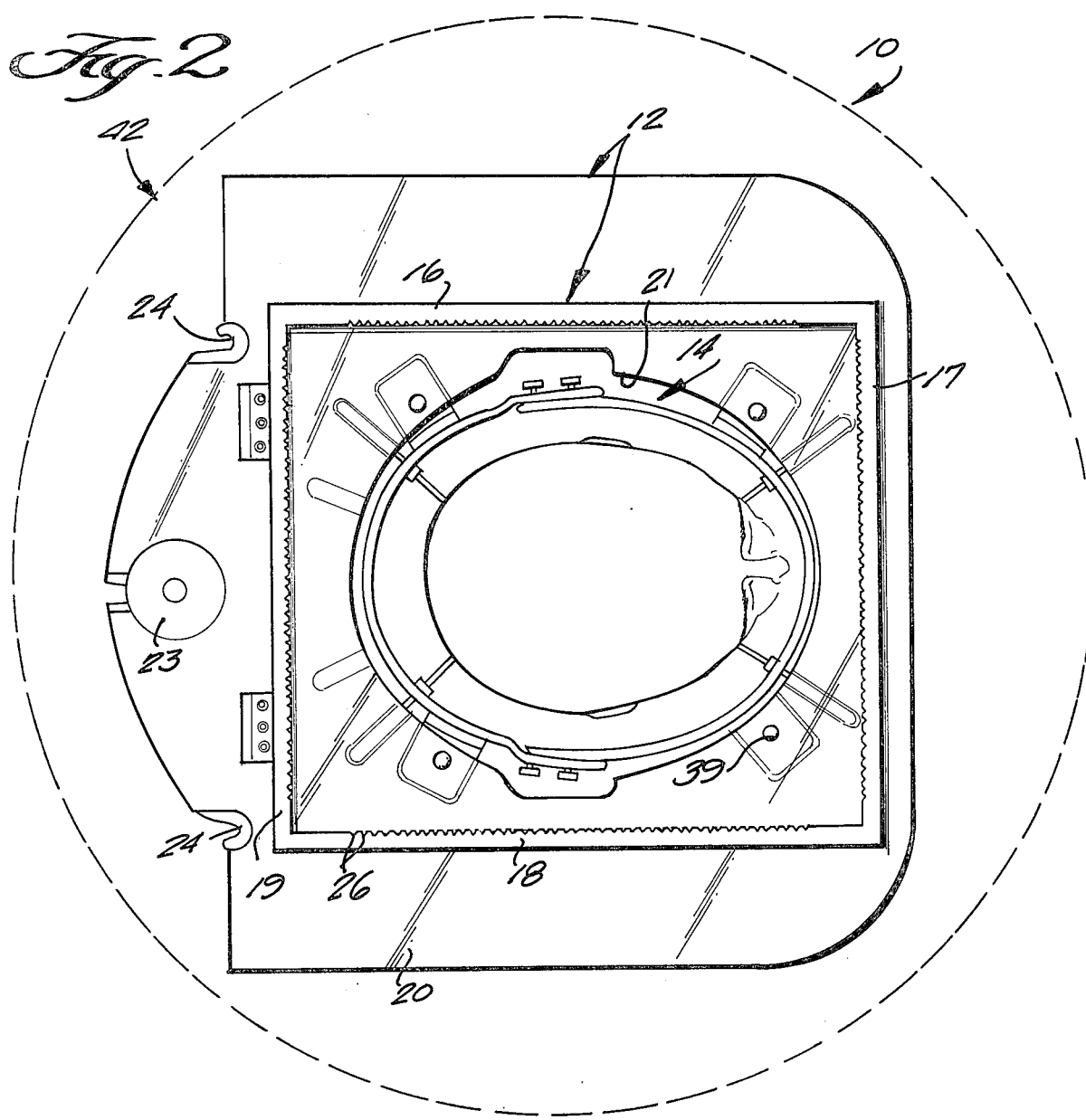
FIG. 2 is a top view of the device of FIG. 1 with one indicia-containing wall in plan and the other wall in top perspective, and shown in schematic association with a CT scanner or a radiotherapy machine.

A stereotaxic device for use in the method, and with the halo assembly, according to the present invention is shown generally by reference numeral 10 in FIGS. 1 and 2, and includes a stereotaxic guide, shown generally by reference numeral 12, and a halo assembly 14 according to the invention. The assembly 14, has means associated therewith for operatively fixing it to the stereotaxic guide 12.

The stereotaxic guide main components comprise a frame, which preferably has four radiolucent substantially planar walls 16, 17, 18, 19 arranged in a quadrate (square) in plan view. A substantially planar base plate 20 is disposed substantially perpendicular to the walls 16 through 19, with means defining a through passage 21 (see FIG. 2) in the base plate 20, interior of a volume defined by the walls 16 through 19, for receipt of the halo assembly 14. The base plate 20 also preferably comprises portions, such as mounting disc 23 and mounting grooves 24, for fixing the frame with respect to a radiotherapy machine, CT scanner, or the like. Such means 23, 24 (see FIG. 2) are disposed exteriorly of the volume defined by the walls 16 through 19.

Each of the walls 16 through 19 include radiopaque indicia means formed thereon. Such indicia means are provided for determining the x, y, and z, coordinates of an intracranial lesion or the like, which ultimately will be treated by radio-therapy. The indicia may take a variety of forms, such as metallic layered strips or the like applied to the walls 16 through 19. A preferred form of the indicia means is illustrated in FIGS. 1 and 2, and comprises a plurality of parallel linear grooves 26 formed in the walls 16 through 19, extending substantially from the bottom to the top thereof, perpendicular to the base plate 20. The grooves are spaced from each other a predetermined distance, a spacing of 5 millimeters being effective. The indicia means further comprises at least one diagonal linear groove formed in each wall 16 through 19, two such diagonal grooves 27 being shown associated with each wall 16 through 19 in the embodiment illustrated in the drawings. In use, the grooves 26 provide x-y location, while the diagonal grooves 27 provide depth (z) location.

The grooves 26, 27 may be formed by any suitable means, such as by machining or etching. The diagonal grooves 27 preferably are disposed in a general V-shape as illustrated in FIG. 1, and are of a greater depth than the parallel grooves 26. While a wide variety of suitable materials are utilizable for the stereotaxic guide 12, one particular useful material is Lucite, or a like transparent hard thermoplastic material. The edges of the grooves 26, 27 are, in practice, radiopaque although the material forming the walls 16 through 19 itself is not. The term "radiopaque" as used in the present specification and claims means that the indicia will show up on a scan display, and thus may be utilized for positively locating the intracranial lesion or the like, which also will show up on the scan display.

The halo assembly 14 according to the invention is shown most clearly in FIGS. 2 and 3. The basic halo assembly is a conventional device commonly utilized for the treatment of cervical fractures. The term "halo assembly" as used in the present specification and claims means such conventional halo assemblies which comprise a relatively narrow width oblong ring component 30 (which may be formed in two parts which are adjustable with respect to each other, and bolted together, as illustrated in FIGS. 2 and 3) with a plurality (e.g. four) of skin penetrating pins 32 extending radially through the ring component 30 and operatively engaging (e.g. by screw-threading) the ring component 30 for positive positioning with respect to the ring component. A special halo assembly according to the invention, shown in FIG. 3 includes—in addition to the conventional halo assembly components—a plurality of brackets, shown generally by reference numerals 34. Each bracket 34 has a first portion 35 thereof affixed (e.g. welded or riveted) to the ring component 30 (such as to the exterior peripheral surface thereof), and a second substantially planar portion 36 extending radially outwardly from the ring component 30. The planar portions 36 of each of the brackets 34 are substantially coplanar and adapted to the be connected to the stereotaxic guide 12.

In the embodiment illustrated in the drawings, each of the second portions 36 of the brackets 34 has a through-extending opening 37 formed therein, which cooperates with a corresponding opening in the base plate 20 through which the shaft of a fastener 39 passes. Each fastener shaft 39 preferably is screw-threaded, as is the interior of each of the openings 37 and the corresponding openings in the base plate (see FIG. 2). The brackets 34, fasteners 39, and base plate 20 with cooperating openings for the fasteners 39 formed therein, collectively comprise means for operatively fixing the position of the halo assembly 14 to the frame walls 16 through 19 to positively position the halo assembly in a predetermined rigid position with respect to the walls 16 through 19. As illustrated in FIG. 2, the upper faces of the second portions 36 of the brackets 34 are preferably disposed flush with the bottom of the base plate 20, with the fasteners 39 extending through each.

The halo assembly 14, being of the type commonly worn by patients with cervical fractures preferably is made of aluminum or other suitable radiolucent material, and once surgically attached by conventional techniques is worn by the patient inbetween treatment sessions. When the halo assembly 14 is fixed with respect to the stereotaxic guide 12, as illustrated in FIG. 2, and the guide 12 is in turn fixed to a CT scanner or radiation therapy machine (shown schematically by reference numeral 42—a typical scanner is illustrated in U.S. Pat. No. 4,002,917), the position of the patient's head with respect to the machine 42 is positively determined.

Operation

In the method of practicing radiotherapy on a patient having an intracranial lesion or the like according to the invention, the approximate position of the intracranial lesion or the like in the patient's head is first determined. This preferably is accomplished utilizing a conventional CT scanner. With this information in mind, the halo assembly 14 is surgically affixed to the patient's head in a position which will ultimately allow proper positioning of the intracranial lesion within the stereotaxic guide 12. The halo assembly 14 is worn by the patient over the entire time period from the first radiotherapy session to the last, the patient being able to function normally with the halo assembly 14 in place.

The halo assembly 14 is positioned in, and fixed to, the stereotaxic guide 12 utilizing the readily releasable fasteners 39, which pass through the openings 27 in brackets 34 and the corresponding openings in the base plate 20 once such openings are aligned. In this position the ring component 30 of the halo extends through opening 21 into the volume defined by the walls 16 through 19. The guide 12 is then fixed in a CT scanner, such as by utilizing mounting disc 23 and mounting grooves 24 associated with base plate 20, and the CT scanner is operated to determine the exact position of the intracranial lesion or the like with respect to the indicia 26, 27 provided by the stereotaxic guide 12.

The stereotaxic guide 12 utilized for diagnosis with the CT scanner preferably has openings formed thereon which allow adjustment of the position of the halo assembly 14 with respect to it. This makes proper location of the intracranial lesion simpler. Ultimately, when the patient goes to a rotational or fixed source radiotherapy machine, a second stereotaxic guide may be utilized—that being of the type illustrated in the drawings— where adjustment between it and the halo assembly 14 is not provided.

Usually the halo assembly 14 will be removed from the stereotaxic guide 12 after the diagnostic scan, and the patient will thereafter immediately (or at some subsequent date) go to a radiotherapy machine. A stereotaxic guide 12 is fixed with respect to the radiotherapy machine, and the coordinates of the intracranial lesion determined from the CT scan are inputted into the radiotherapy machine. The proper positioning of the radiotherapy machine (i.e. the treatment source thereof) with respect to the intracranial lesion is tested utilizing a target device mounted in the stereotaxic guide, and the relative position of the radiotherapy machine is adjusted if necessary.

Figure 4:
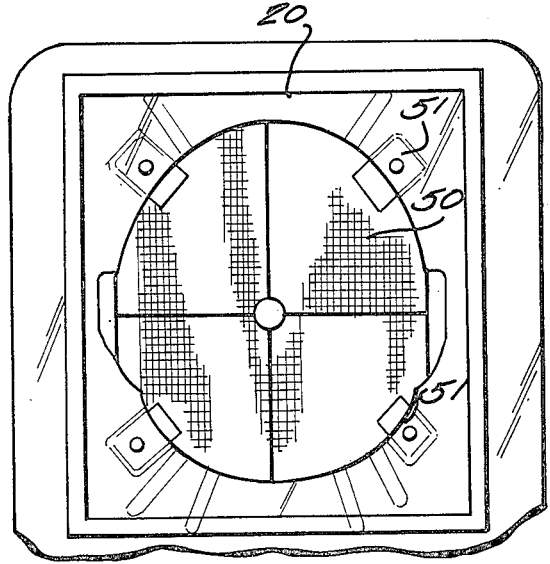
FIG. 4 is a top plan view of a stationary target member in association with the stereotaxic guide of FIGS. 1 and 2.

A typical target device is illustrated in FIGS. 4 and 5, and includes a stationary base 50 (see FIG. 4) having x and y coordinates thereon, and radially extending brackets 51 which cooperate with the base plate 20 of the stereotaxic guide 12 in the same manner that brackets 42 cooperate with it. A movable target member 53, including a magnetized base 54 which is mounted on the target plate 50, is movable to the appropriate x,y coordinate. An actual target component 55 of the movable target member 53 is vertically positionable on the shaft 56 of the device 53 to determine the z coordinate. The component 55 is moved to the appropriate x, y, z coordinates for the intracranial lesion, the radiotherapy machine is actuated, and the position is tested.

Once it is determined that the radiotherapy machine is operating properly, the target device is removed and the patient's halo assembly 14 is mounted in the stereotaxic guide 12 and the radiotherapy machine is operated to provide one treatment session for the patient. Note that the patient's head will be positioned in the stereotaxic guide and in the radiotherapy machine so that the treatment radiation is applied to the intracranial lesion. In this manner an extremely accurate treatment can be provided, with treatment of intracranial lesions on the order of 4×4 centimeters being possible.

Once one treatment session is completed, the halo assembly 14 is removed from the stereotaxic guide, and the patient is free to move about. When the patient ultimately returns for the next treatment session, the halo assembly 14 is again fixed in the stereotaxic guide 12, and the treatment steps (including testing) practiced in the first treatment session are repeated. Each session follows the same procedures until finally all radiotherapy sessions for the patient are completed, at which time the halo assembly is surgically removed from the patient's head.

It will thus be seen that according to the present invention a simple yet effective method of practicing radiotherapy on a patient having an intracranial lesion or the like, has been provided. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and methods.

What is claimed is:

1. A stereotaxic device comprising:
   a frame, having four radiolucent substantially planar walls arranged in a quadrate in plan view;
   radiopaque indicia means formed on said walls;
   a portable and wearable halo assembly comprising a ring component and a plurality of skin-penetrating pins extending radially through said ring component and operatively engaging said ring component for positive positioning with respect thereto;
   means for operatively fixing the position of said halo assembly to said frame walls to positively position the halo assembly in a predetermined position with respect to said walls; and
   means for fixing said frame with respect to a radiotherapy machine.

2. A device as recited in claim 1 wherein said frame includes: a substantially planar base plate substantially perpendicular to said walls; and means defining a through passage in said base plate, interior of a volume defined by said walls, for receipt of said halo assembly.

3. A device as recited in claim 2 wherein said means for operatively fixing the position of said halo assembly to said frame comprises: a plurality of brackets attached to said halo assembly, each bracket having a substantially planar portion extending generally perpendicular to the ring component of said halo assembly, with the planar portions of all brackets being substantially coplanar; and releasable fastening means for fastening said brackets to predetermined portions of said base plate with the halo ring component received within said through-extending opening in said base plate.

4. A device as recited in claim 3 wherein said fastening means comprises: means defining a through-extending opening in each of said bracket planar portions; means defining a through-extending opening in said base plate for cooperation with each of said bracket openings; and a plurality of fasteners each having a shaft extending through one of said bracket and base plate set of openings for fixing each bracket to said base plate.

5. A method of practicing radiotherapy on a patient having an intracranial lesion or the like, comprising the steps of sequentially:
   (a) determining the approximate position of the intracranial lesion or the like in the patient's head;
   (b) surgically affixing a halo assembly to the patient's head to be maintained in place until all radiotherapy sessions for the patient are completed, taking care to position the ring component of the halo assembly with respect to the patient's skull so that effective treatment with radiation will be practiced;
   (c) positioning the halo assembly in, and fixing it to, a stereotaxic guide having radiopaque indicia associated therewith;
   (d) fixing the stereotaxic guide in a CT scanner;
   (e) operating the CT scanner to determine the exact position of the intracranial lesion or the like with respect to the indicia provided by the stereotaxic guide;
   (f) transferring the patient to a radiotherapy machine;
   (g) fixing the stereotaxic guide with respect to the radiotherapy machine;
   (h) inputting the coordinates of the intracranial lesion or the like determined from the CT scan to the radiotherapy machine;
   (i) operating the radiotherapy machine to provide one treatment session for the patient, positioned in the stereotaxic guide in the radiotherapy machine;
   (j) removing the halo assembly from the stereotaxic guide;
   (k) replacing the stereotaxic guide on the halo assembly when the patient returns for the next treatment session, the halo assembly remaining in place on the patient between treatment sessions;

(l) repeating steps (g)–(k) until all desired radiotherapy sessions for the patient are completed; and (m) removing the halo assembly from the patient's head.

6. A method as recited in claim 5 comprising the further step of, between steps (f) and (g), (n) removing the patient from the stereo-taxic guide; and comprising the further steps of, between steps (g) and (i), (o) testing proper position of the radiotherapy machine with respect to the intracranial lesion or the like utilizing a target device in the stereotaxic guide, and adjusting the relative position of the radiotherapy machine if necessary; and (p) fixing the halo assembly in the stereotaxic guide; and wherein step (l) further comprises repeating steps (n)–(p) for each session.

* * * * *